United States Patent [19]

Hemler et al.

[11] Patent Number: 5,527,679
[45] Date of Patent: Jun. 18, 1996

[54] β₅ PROTEIN AND DNA ENCODING THE SAME

[75] Inventors: Martin E. Hemler, Auburndale, Mass.; Hemavathi Ramaswamy, New Haven, Conn.

[73] Assignee: Dana Farber Cancer Institute, Boston, Mass.

[21] Appl. No.: 54,077

[22] Filed: Apr. 27, 1993

Related U.S. Application Data

[62] Division of Ser. No. 694,314, May 1, 1991, abandoned.

[51] Int. Cl.⁶ .......................... C12Q 1/68; G01N 33/53; C07H 21/04; C12N 15/00
[52] U.S. Cl. ................. 435/6; 435/7.1; 435/968; 436/501; 436/503; 436/504; 436/815; 536/23.1; 536/23.5; 536/24.31; 935/76; 935/77; 935/78
[58] Field of Search ........................ 435/7.1, 6, 7.21, 435/7.94, 7.5, 968; 536/23.5, 24.31, 23.1; 935/78, 76, 77; 436/501, 503, 504, 815

[56] References Cited

U.S. PATENT DOCUMENTS 4,755,458  7/1988  Rabbani et al. .......................... 435/5

OTHER PUBLICATIONS

Cheresh et al., Cell, vol. 57, pp. 59–69, Apr. 7, 1989.
Krontiris et al, *Journal of Cellular Biochemistry*, vol. 30, pp. 319–329 (1986).
Oellerich, *J. Clin. Chem. Clin. Biochem.*, vol. 22, 1984, pp. 895–904.
Sommer, et al., *Nucleic Acids Research*, vol. 17, No. 16, 1989, p. 6749.
Suzuki et al, ; sequence comparison; PNAS, U.S.A., vol. 87, pp. 5354–5358 (1990).
Gingsberg, et al. *Thrombos. Hemostats.* 59:1–6 (1988).
Hemler, et al. *Annu. Rev. Immunol.* 8:365–400 (1900).
Hemler, et al., *J. Biol. Chem.* 264:6529–6535 (1989).
Kajiji, et al., *Cancer Res.* 47:1367–1376 (1987).
Kajiji, et al., *EMBO J.* 8:673–680 (1989).
Kishimoto, et al., *Adv. Immunol.* 46:149–182 (1989b).
Argraves, et al., *J. Cell. Biol.* 105:1183–1190 (1987).
Elices, et al., *Cell* 60:577–584 (1990).
Fitzgerald, et al., *J. Biol. Chem.* 262:3936–3939 (1987).
Freed, et al., *EMBO J.* 8:2955–2965 (1989).
Holers, et al., *J. Exp. Med.* 169:1589–1605 (1989).
Holzmann, et al., *Cell* 56:37–46 (1989).
Holzman and Weismann, *EMBO J.* 8:1735–1741 (1989).
Kishimoto, et al. *Cell* 48:681 (1987).
Law, et al. *EMBO J.* 6:915–919 (1987).
Tamkun, et al. *Cell* 46:271–282 (1986).
Tominaga, *FEBS Letters* 238:315–319 (1988).
D'Souza, et al., *Science* 242:91–93 (1988).
Desimone and Hynes, *J. Biol. Chem.* 263:5333–5340 (1988).
Falcioni, et al., *Cancer Res.* 46:5772–5778 (1986).
Horwitz, et al., *Nature* 320:531–533 (1987).
Kimmel and Carey, *Cancer Res.* 46:3614–3623 (1986).
Smith and Cheresh, *J. Biol. Chem.* 263:18726–18731 (1988).
Ramaswamy and Hemler, *The EMBO Journal* 9(5):1561–1568 (1990).
Argraves, et al., *Cell* 58:623–629 (1989).
Ruoslahti, *Annu. Rev. Biochem.* 57:375–413 (1988).
Rosa, et al., *Blood* 72:593–600 (1988).
Cheresh, et al., *Cell,* 57:59–69 (1989).
Wayner, et al., *Journal of Cell Biology,* 113:919–929 (1991).
McLean, et al., *J. Bio. Chem.* 265:17126–17131 (1990).
Smith, et al., *J. Biol. Chem.* 265:11008–11013 (1990).

*Primary Examiner*—W. Gary Jones
*Assistant Examiner*—Bradley L. Sisson
*Attorney, Agent, or Firm*—David G. Conlin; David S. Resnick; Ronald I. Eisenstein

[57] ABSTRACT

In accordance with the present invention, a cDNA clone encoding a new human β subunit which was designated β₅ was found. Probes for this nucleotide sequence are described. In addition, the β₅ protein, its associated subunit and its cell distribution were characterized. In another embodiment, this invention relates to assays for detecting this protein. β₅ subunit was found present on carcinomas, but absent from lymphoid cells. Consequently, this protein can be used to determine the presence of carcinoma.

13 Claims, 7 Drawing Sheets

```
BETA1      GACCTCTACTACCTTATGGACCTGTCTTATTCAATG
BETA2      GACCTGTACTATCTGATGGACCTCTCCTACTCCATG
BETA3      GACATCTACTACTTGATGGACCTGTCTTACTCCATG
BETA5      GACCTGTACTACCTGATGGACCTCTCCCTGTCCATG

OLIGO # 1    GACCTCTACTACCTGATGGACCT     (23-mer, 32-fold degenerate)
                 A G    TT T OLIGO # 2              ATGGACCTGTCTTACTCCATG   (21-mer, 16-fold degenerate)
                           C  C  T A
```

```
GGGGACAACTGTAACTGCTCGACAGACATCAGCACACATGCCGGGCAGAGATGGCCAGATCTGCAGCGAGCGTGGGCACTGTCTCTGTGGGCAGTGCCAA   2178
 G  D  N  C  N* C  S  T  D  I  S  T  C  R  G  R  D  G  Q  I  C  S  E  R  G  H  C  L  C  G  Q  C  Q     591
TGCACGGGAGCCCGGGGGCCTTTGGGGAGATGTGTGAGAAGTGCCCAAGCATGCAGCAGAGATTGCGTGAGTGCCTGCTGCTC                    2277
 C  T  E  P  G  A  F  G  E  M  C  E  K  C  P  T  C  P  D  A  C  S  T  K  R  D  C  V  E  C  L  L  L    624
CACTCTGGGAAACCTGACAACCAGAACCTGCCACAGCCTATGCAGGATGAGGTGATCACATCGTGAAAGATGACCAGGAGGCTGTG                2376
 H  S  G  K  P  D  N* Q  T  C  H  S  L  C  R  D  E  V  I  T  W  V  D  T  I  V  K  D  D  Q  E  A  V    657
CTATGTTTCTACAAAACCGCCAAGGACTGCGTCATGATGTTCACCTATGTGGAAGCTCCCCAGTGGAAGTCCAACCTGACCGTCCTCAGGGAGCCAGAG    2475
 L  C  F  Y  K  T  A  K  D  C  V  M  M  F  T  Y  V  E  L  P  S  G  K  S  N* L  T  V  L  R  E  P  E    690
TGTGGAAACACCCCCAACGCCATGACCATCCTCCTGGCTGTGGTCAGCATCCTCCTTGTTGGGCTTGCACTCCTGGCTATCTGGAAGCTGCTTGTC       2574
 C  G  N  T  P  N  A  M  T  I  L  L  A  V  V  S  I  L  L  V  G  L  A  L  A  I  W  K  L  L  V           723
ACCATCCACGACCGGAGGGAGTTTGCAAAGTTTCAGAGGAGCCGAGCGATCCAGGGCCCGCTATGAAATGGCTTCAAATCCATTATACAGAAAGCCTATCTCC  2673
 T  I  H  D  R  R  E  F  A  K  F  Q  S  E  R  S  R  A  R  Y  E  M  A  S  N  P  L  Y  R  K  P  I  S    756
ACGCACACTGTGGACTTCACCTTCAACAAGTTCAACAAATCCTACAATGGCACTGTGGACTGTGACTGATGTTTCCTTCTCCGAGGGGCTGAGCGGGATCTGA  2772
 T  H  T  V  D  F  T  F  N  K  F  N* K  S  Y  N* G  T  V  D                                            776
TGAAAAGGTCAGACTGAAACGCCTTGCACGGCTTGCTCGGCTTGATCACAGCTCCCACAGAGAAGACCTTCTAGTGAGCTGGGCCAG               2871
GAGCCCACAGTGCTGTACAACAAGGGAAAGGTGCCTGGCCATGTCACCTGGCTGCCAGAGCCATGCCAGTTCGCGTCCCTAAGAGCTTGGGATA        2970
AAGCAAGGGGACCTTGGCGCTCTCAGCTTTCCCTGCCACATCCAGGAAGGTCGGAGTCTGTAAAACCAGTGAGATGCTGGGCTTTGGCTTTTCACATTGATCATTTTA  3069
CGTGGGCCCCAAATAAAAAGATCCTGCATTATGGTGTAGTTCTGAGTCTGAGATGTGTATGCCTGATGCTATGCCTTGCACACAGGTGTTGGTGATGGGCTG  3168
TATGAAATAAAGATTGTTGAAGGTACATCGTTTGCAAATGTCAGTTCTCAGGAATTGGTGTTATGGGCTG                                3267
TTGAGATGCCTGTTGAAGGTAAAGATTAAAACCAAAGAATTTGTTTGTTTGTTTGCTGCCC                                          3366
GGGATTGGAAGTAAAGATTAAAACCAAAGAATTTGTGTTTGTCTGCCC                                                      3415
```

FIG. 4B

FIG. 5

# $\beta_5$ PROTEIN AND DNA ENCODING THE SAME

This is a divisional of application Ser. No. 07/694,314 filed on May 1, 1991, abandoned.

BACKGROUND OF THE INVENTION

This invention relates to a novel human integrin β subunit protein, $\beta_5$, DNA encoding this protein, and to methods for detection and/or quantification of $\beta_5$. In one embodiment this includes detecting $\beta_5$ protein in the biological fluids or tissues of humans using antibodies which are capable of binding to this protein.

The integrin family consists of at least 14 distinct cell surface heterodimers that are involved in cell-cell and cell-extracellular matrix adhesion functions (Ginsberg, et al., (1988) *Thrombos. Hemostas.*, 59:1–6); Kishimoto, et al., (1989b) *Adv. Immunol.*, 46:149–182; Ruoslahti, (1988) *Annu. Rev. Biochem.*, 57:375–413; Hemler, (1990) *Annu. Rev. Immunol.*, 8:365–400). The integrins were originally divided into three subfamilies, each having a characteristic β chain that associates with multiple α subunits (Hynes, (1987) *Cell*, 48:549–554). The VLA protein family (sharing a common $\beta_2$ subunit) has three members involved in leukocyte cell-cell adhesion (Kishimoto, et al., (1989b) *Adv. Immunol.*, supra); and the cytoadhesion family (sharing the $\beta_3$ subunit) consists of the platelet IIb-IIIa complex and the vitronectin receptor, which adhere to a variety of extracellular matrix proteins (Ginsberg, et. al., (1988) *Thrombos. Hemostas.*, supra).

Recently, the discovery of additional β subunits has added to the complexity within the integrin family. For example, the $\alpha^6$ subunit associates not only with $\beta_1$, but also with a newly described $\beta_4$ subunit (Hemler, et al., (1989) *J. Biol. Chem.*, 264:6529–6535; Kajiji et al., (1989) *EMBO J.*, 8:673–680). Compared to $\alpha^6\beta$, which has widespread distribution, $\alpha^6\beta_1$ is prevalent on normal neoplastic epithelial cell types (Hemler, et al., (1989) *J. Biol. Chem.*, supra) and aligns with basement membranes in many tissues (Kajiji, et al., (1987) *Cancer Res.*, 47:1367–1376). Similarly, on a subset of mouse lymphocytes, the mouse $\alpha^4$ subunit associated with $\beta_p$ instead of $\beta_1$, and the $\alpha^4\beta_p$ complex functions as a receptor for high endothelial venules in Peyer's patches (Holzmann, et al., (1989) *Cell*, 56:37–46; Holzmann and Weissman, (1989) *EMBO J.*, 8:1735–1741). While the $\alpha^4\beta_1$ (VLA-4) complex might also bind to Peyer's patches (Holzmann and Weissman, (1989) *EMBO J.*, supra), it has multiple other adhesive functions (Elices, et al., (1990) *Cell*, 60:577–584). The $\alpha^v$ subunit of the vitronectin receptor has reported to associate with two additional β subunits besides $\beta_3$. A complex called $\alpha^v\beta_x$ was identified from lung carcinoma cells, using an anti-$\alpha^v$ monoclonal antibody (mAb) (Cheresh, et al., (1989) *Cell*, 57:59–69). The $\beta_x$ subunit was chemically distinguishable from the $\beta_3$ subunit which is usually associated with $\alpha^v$ on endothelial cells and other cell types (Cheresh, et al., (1989) *Cell*, supra). However, the $\beta_x$ subunit has not been fully elucidated. On MG63 osteosarcoma cells and fibroblasts, a subunit called $\beta_s$ was found to be associated with $\alpha^v$, and the $\beta_s$ subunit underwent a marked serine phosphorylation upon treatment of MG63 cells with a tumor promoter PMA (Freed, et al., (1989) *EMBO J.*, 8:2955–2965). Although $\beta_s$ is antigenically and biochemically distinct from $\beta_3$, it is not yet certain that it is distinct from $\beta_x$. One problem has been that neither cDNA probes nor antibody reagents have been available for use in direct characterization of $\beta_x$ (or $\beta_s$).

At this time the $\beta_p$, $\beta_4$, $\beta_x$ (and $\beta_s$) subunits each are known to associate with only one known α subunit, and thus do not appear to define new integrin families. Instead, they replace the prototype $\beta_1$ and $\beta_3$ heterodimers on certain cell types.

Among the β subunits, genes for human $\beta_1$ (Argraves, et al., (1987) *J. Cell Biol.*, 105:1183–1190), $\beta_2$ (Kishimoto, et al., (1987) *Cell*, 48:681–690; Law, et al., (1987) *EMBO J.*, 6:915–919) and $\beta_3$ (1988) *Blood*, 72:593–600 have been cloned and sequenced, and show 44–47% homology to each other, with complete conservation of all of their 56 cysteines. Also, the $\beta_1$ subunits from human (Argraves, et al., (1987) *J. Cell Biol.*, supra. mouse (Tominaga, (1988) *FEBS Letters*, 238:315–319); Holers, et al., (1989 *J. Exp. Med.*, 169:1589;14 1605) chicken (Tamkun, et al., (1986) *Cell*, 46:271–282) and frog (Desimone and Hynes, 1988) *J. Biol. Chem.*, 263:5333–5340) show 82–90% homology, emphasizing the importance of this molecule throughout vertebrate evolution.

From their primary structures, it is evident that each of the integrin β subunits is a transmembrane protein, with a large extracellular domain and a short cytoplasmic tail. Within the extracellular domain, the region near amino acids 100–140 has a particularly high degree of conservation. In addition, RGD-peptide crosslinking studies have implicated that same region as a potential ligand binding site (D'Souza, et al., (1988) *Science*, 242:91–93; Smith and Cheresh, (1988) *J. Bio. Chem.*, 263:18726–18731).

The cytoplasmic domain of $\beta_1$ has been shown to bind to the cytoskeletal protein talin (Horwitz, et al., (1987) *Nature*, 320:531–533) and a newly described protein called fibulin (Argraves, et al., (1989) *Cell*, 58:623–629). These cytoskeletal interactions may be critical for the function of integrins as transmembrane receptors, linking extracellular matrix ligands with the cytoskeletal framework. The cytoplasmic domains of the known β subunits are highly dissimlilar, suggesting that each interacts with the cytoskeleton in a specific manner.

Several β subunits have been found associated with carcinomas. Specifically, the expression of $\beta_4$ in mouse (Falcioni et al., (1986) *Cancer Res.*, 46:5772–5778) and human cells (Kimmel and Carey, (1986) *Cancer Res.*, 46:3614–3623) has been correlated with tumor cell aggressiveness.

It would be useful to have an additional determinant for detecting the presence of carcinomas.

In addition, it would be useful to have a means by which to distinguish different cell types.

SUMMARY OF THE INVENTION

In accordance with the present invention, a cDNA clone encoding a new human β subunit which was designated $\beta_5$ was found. Probes for this nucleotide sequence are described. In addition, the $\beta_5$ protein, its associated subunit and its cell distribution were characterized. In another embodiment, this invention relates to assays for detecting this protein. $\beta_5$ subunit was found present on carcinomas, but absent from lymphoid cells. Consequently, this protein can be used to determine the presence of carcinoma.

BRIEF DESCRIPTION OF THE FIGURES

FIG. 1 presents the design of oligonucleotide probes used for selecting a new integrin β subunit.

3

Figure 2:
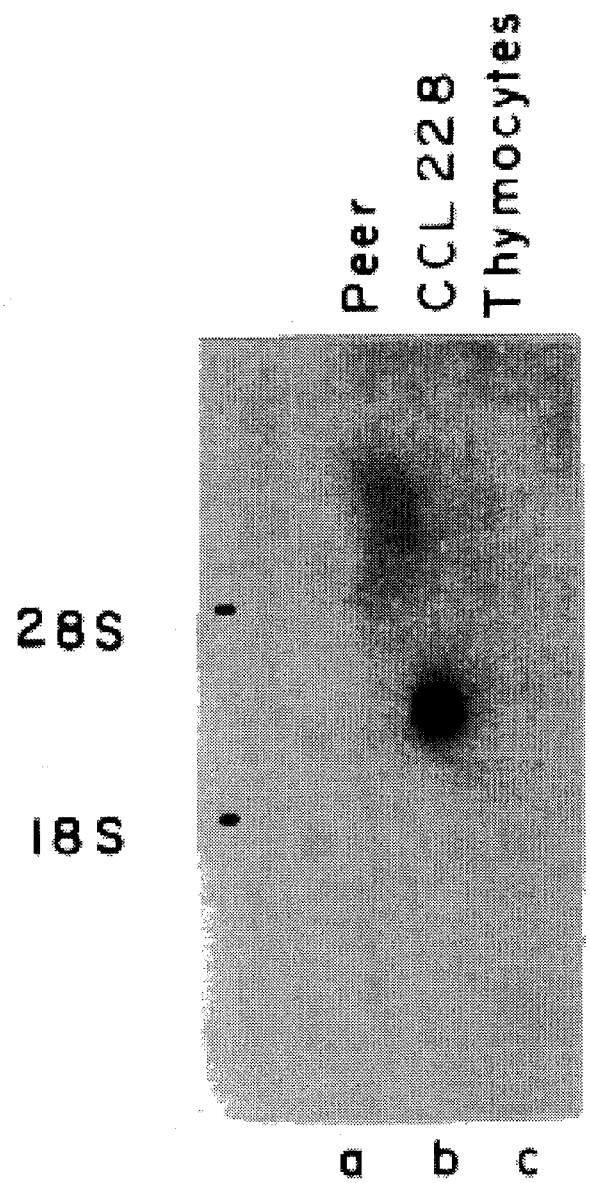

FIG. 2 shows a Northern blot analysis of $\beta_5$ message. Total RNA from the leukemic cell line PEER, the colon carcinoma cell line CCL 228 and from normal human thymocytes (10 µg/lane) was separated by electrophoresis under denaturing conditions, and probed with a 1.8 kb SphI fragment of cDNA derived from $\beta_5$ clone 9.2.

Figure 3:
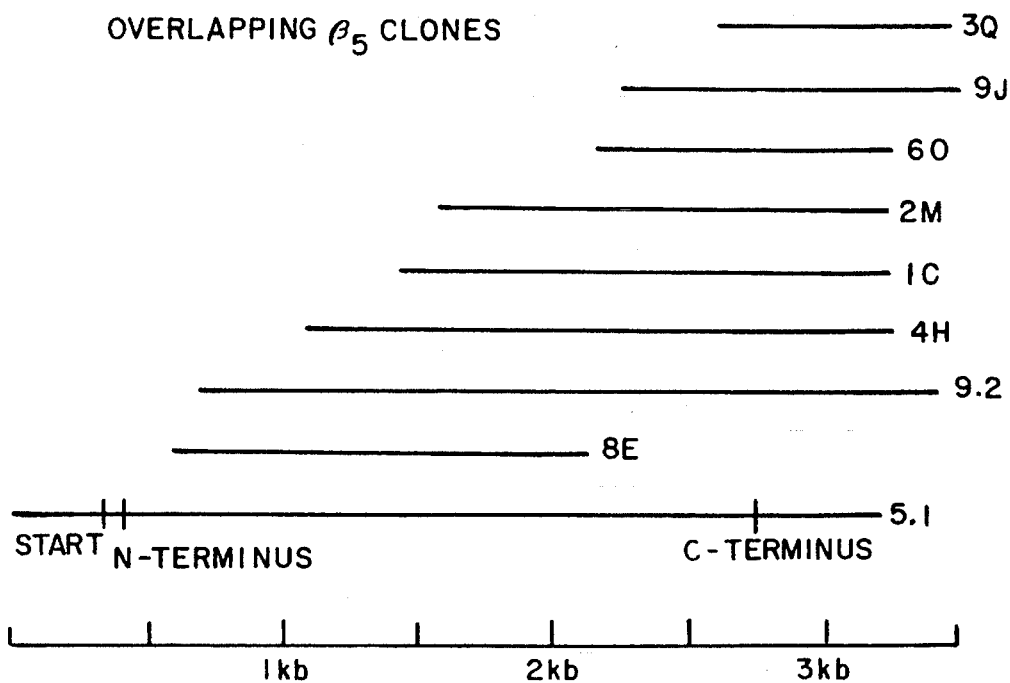

FIG. 3 shows the alignment of overlapping $\beta_5$ cDNA clones. The nine clones indicated have essentially the same sequences, except that the polyadenylation site observed in clone 60 is replaced by −200 bp of unknown sequence in clones 9.2, 9J and 3Q. Other variations between clones are listed in Table II.

Figure 4A:
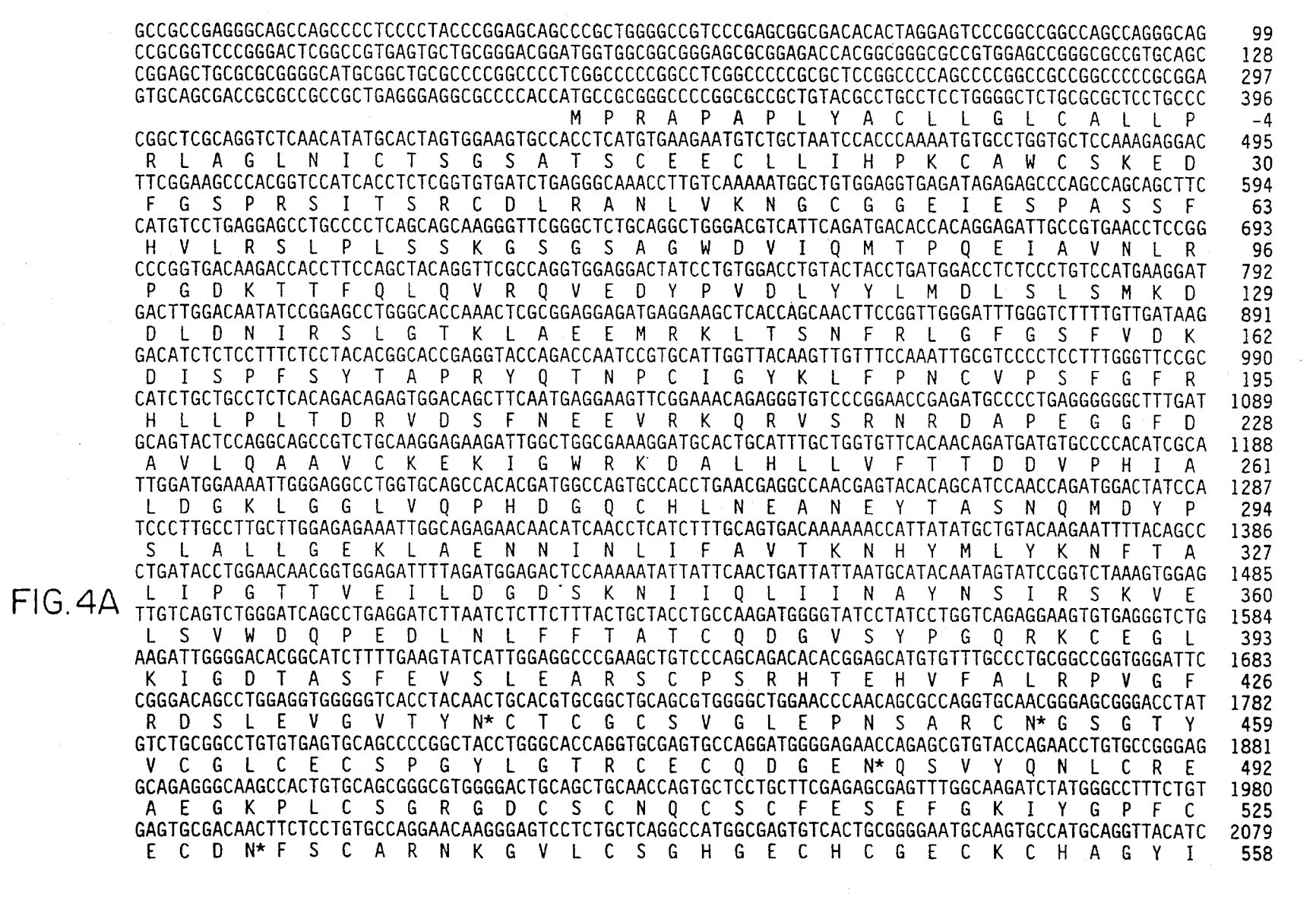

FIGS. 4A and 4B show the complete nucleotide sequence (SEQ ID NO:1) and the deduced amino acid sequence (SEQ ID NO:2) of human $\beta_5$ cDNA. The sequence is taken from clone 5.1. The putative N-terminus is indicated with an arrow. The transmembrane domain is underlined and the potential N-glycosylation sites are marked with *. The signal for a poly(A) tail is underlined. Although not found in clone 5.1, a poly(A) tail was found in clone 60, −20 bp after the poly(A) signal.

Figure 5:
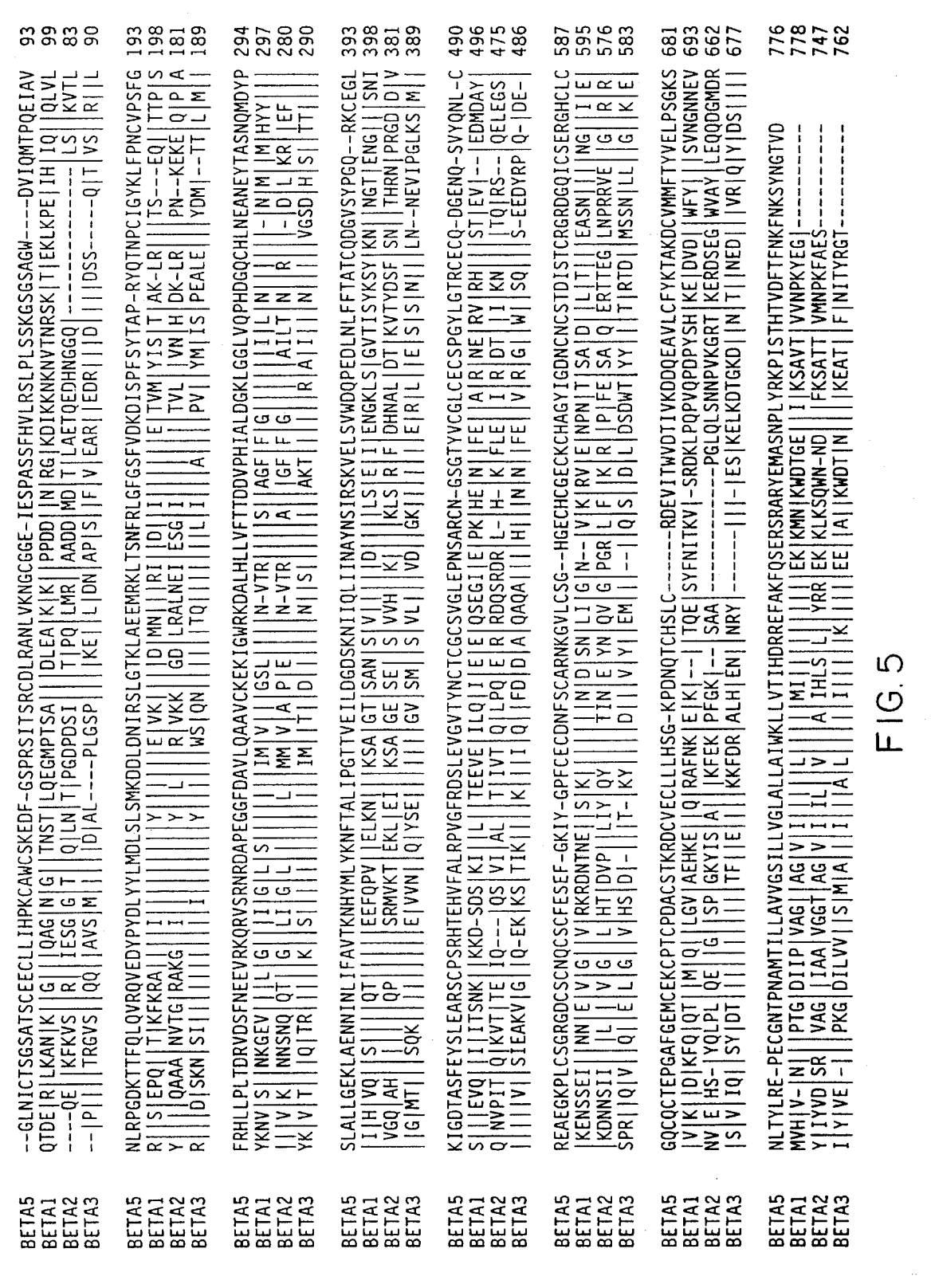

FIG. 5 shows the alignment of $\beta_5$ and other human integrin $\beta$. The protein sequences of $\beta_1$ (Argraves, et al., (1987) *J. Cell Biol.*, supra), $\beta_2$ (Kishimoto, et al., (1987) *Cell*, supra; Law, et al., (1987) *EMBO J.*, supra) and $\beta_3$ (Fitzgerald, et al., (1987) *J. Biol. Chem.*, supra; Rosa, et al., (1988) *Blood*, supra) are compared with that of $\beta_5$. The shared amino acids are indicated by vertical lines with the $\beta_1$, $\beta_2$, $\beta_3$ sequences. Gaps (−) are introduced to maximize alignment.

Figure 6:
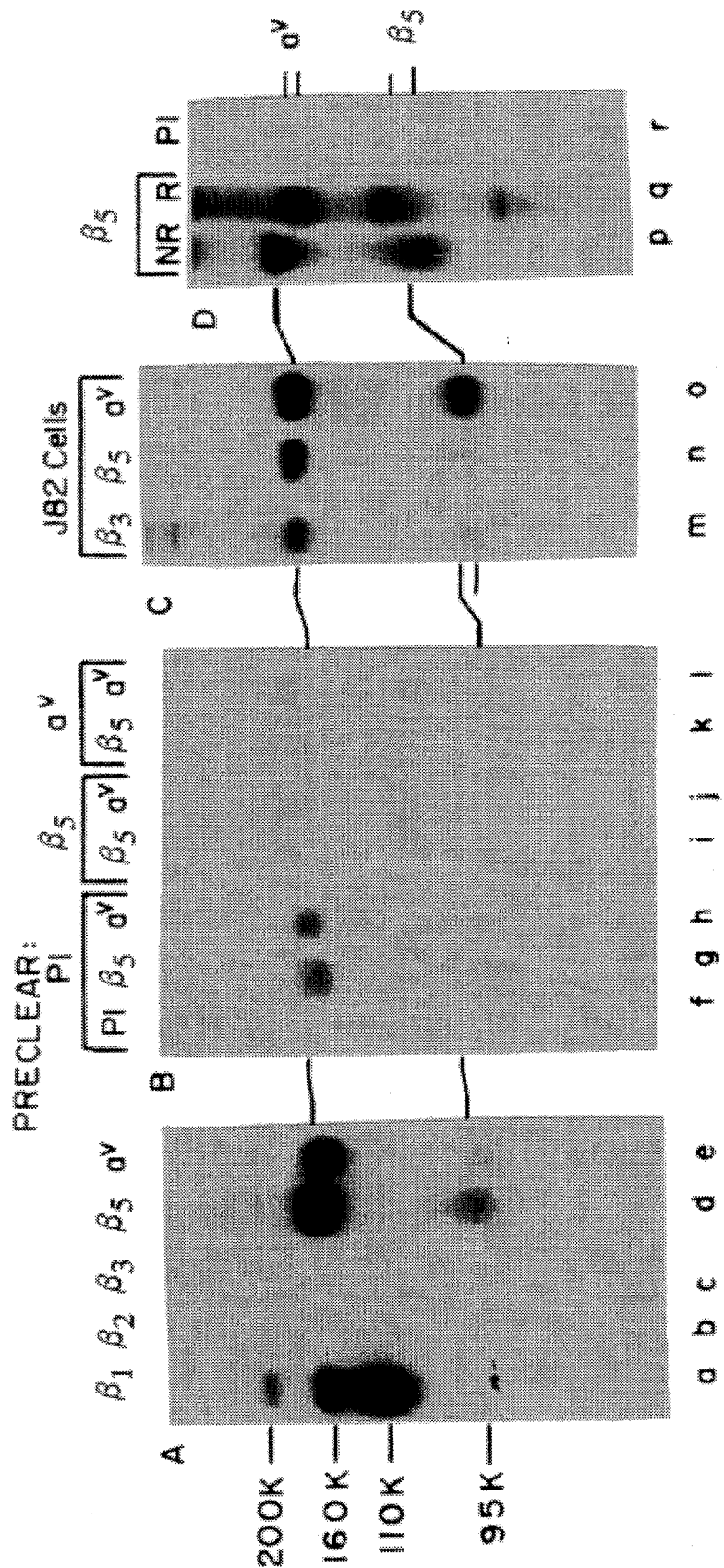

FIG. 6 is a characterization of the $\beta_5$ protein and its associated $\alpha$ subunit. (A) $^{125}$I-surface labeled CCL 228 cell extract was immunoprecipitated with monoclonal antibodies A-1A5 (lane a). TS1/18 (lane b), mAb 15 (lane c), rabbit anti-$\beta_5$ C-terminal peptide (lane d) and LM142 (lane e). (B) The CCL 228 extract was depleted of $\beta_5$ by pre-clearing with anti-$\beta_5$ C-peptide antiserum and then precipitated with the anti-$\beta_5$ antiserum (lane i) or with mAb LM142 (lane j). LM142 was also used for immunodepletion of $\alpha^V$ subunit from CCL 228 extract, followed by immunoprecipitation with anti-$\beta_5$ C-peptide antiserum (lane k) or with LM142 (lane l). Control pre-clearing was performed using pre-immune rabbit serum followed by precipitation with the same pre-immune serum (lane f), anti-$\beta_5$ C-peptide (lane g) or LM142 (lane h). (C) $^{125}$I-surface-labeled J82 cell extract was immunoprecipitated with mAb 15 (lane m), anti-$\beta_5$ C-peptide antiserum (lane n) or LM142 (lane o). (D) The mobility of $\beta_5\alpha^V$ was determined by SDS-PAGE under non-reducing (lane p) and reducing (lane q) conditions. Control precipitation was done with rabbit pre-immune serum (lane r).

Figure 7:
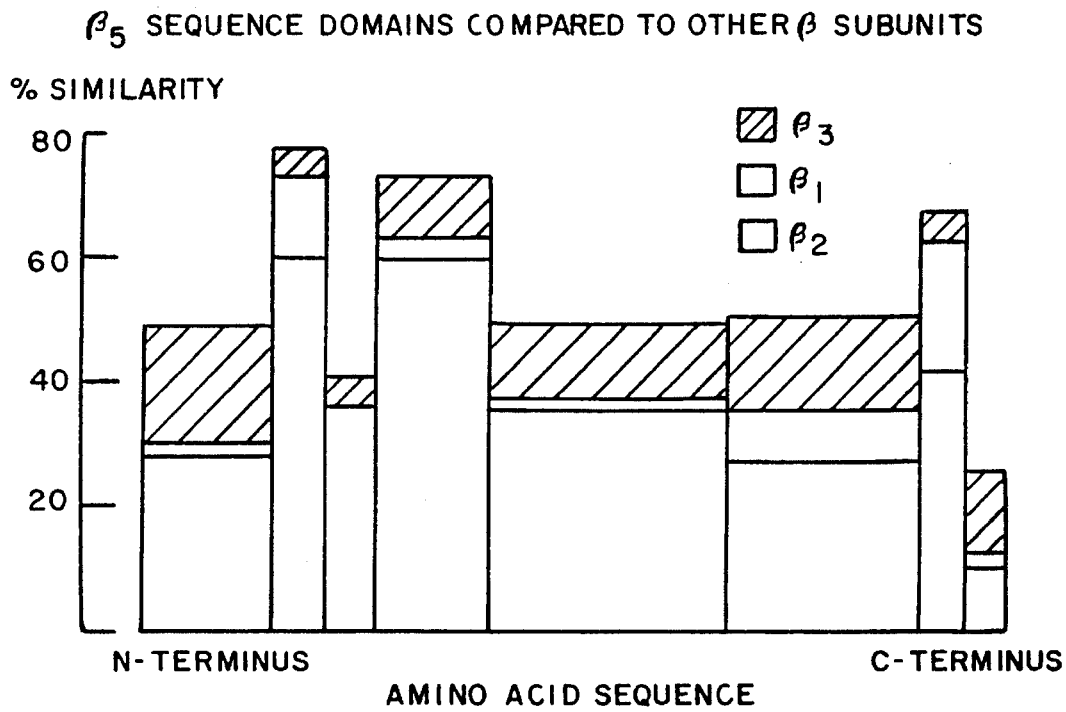

FIG. 7 presents a comparison of sequence domains in $\beta_5$ and other integrin $\beta$ subunits. The amino acid sequence of $\beta_5$ was compared with other $\beta$ subunit sequences based on the alignment shown in FIG. 5. Domains of $\beta_5$ were divided into segments from amino acids 1–112, 113–162, 163–206, 207–315, 316–528, 529–694, 695–737 and 738–776.

DETAILED DESCRIPTION OF THE INVENTION

A human integrin $\beta$ subunit protein, named $\beta_5$, has been cloned, sequenced and found to be distinct from all other known $\beta$ subunits. An anti-$\beta_5$ rabbit serum was prepared against a synthetic C-terminal peptide of $\beta_5$, and this serum was used to directly demonstrate that (i) $\beta_5$ is a 95,000–100, 000 $M_r$ cell surface protein and (ii) that $\beta_5$ associates with the previously described integrin $\alpha^V$ subunit, but no other detectable $\alpha$ subunit.

The term "substantially purified" means synthesized or, if naturally occurring, isolated free of other cellular components with which it is normally associated. Preferably, the protein has been purified to at least about 85% pure, more preferably to at least 95%, and most preferably to at least 99%.

While the function of human integrin $\beta_5$ subunit protein in normal growth and differentiation of cells appears to be related to a matrix-adherence functions, it appears that the protein encoded by the human integrin $\beta_5$ gene might play an important role in tumor cell aggressiveness and in the initiation or progression of neoplastic transformation.

One embodiment concerns a integrin $\beta_5$ subunit protein which is detectable in a human biological fluid such as blood, serum, plasma, urine, cerebrospinal fluid, supernatant from normal cell lysate, supernatant from preneoplastic cell lysate, supernatant from neoplastic cell lysate, supernatants from carcinoma cell lines maintained in tissue culture, and breast aspirates.

Another embodiment concerns probes to the $\beta_5$ nucleotide sequence, which are preferably found in tissue samples. These probes can be RNA or DNA probes. Preferably, the probe is to the $\beta_5$ protein encoding nucleotide sequence or a fragment thereof.

More specifically, this invention concerns a substantially purified $\beta_5$, which is a cell surface protein having a molecular weight in the range from about 95,000 daltons to about 100,000 daltons and associates with the integrin $\alpha^V$ subunit. Preferably thee is no more than about 5%, no other detectable $\alpha$ subunit as determined by an immuno-preciptitation format. More preferably there is no detectable $\alpha$ subunit.

The term "corresponds substantially" provides for conservative additions, deletions and/or substitutions.

The molecular weight range of $\beta_5$ was determined using an immunoprecipitation format as described below.

This invention also concerns a method of detecting pre-neoplastic or neoplastic cells in a human which comprises testing a biological fluid from a human for the presence of a $\beta_5$ by:

(a) contacting the fluid with at least one probe, for example a DNA probe or a monoclonal antibody, which is capable of binding the nucleotide sequence or the protein, and (b) determining whether binding has occurred.

In other embodiment this invention concerns an immunoassay for detecting or quantifying the presence of $\beta_5$ which comprises:

(a) reacting the fluid with at least one first antibody, preferably a monoclonal antibody, which is capable of binding to $\beta_5$;

(b) reacting the product of step (a) with at least one detectably-labeled second antibody which is capable of binding to $\beta_5$ at an epitope different from the epitope bound by the first antibody; and (c) detecting or quantifying the product of step (b).

The antibodies which can be used to detect $\beta_5$ constitute another aspect of this invention. Preferably, the antibodies are monoclonal antibodies.

Immunoreactive fragments of these antibodies can also be used to practice the invention.

In an alternative embodiment one can prepare the antibody in a host animal other than the individual to be treated.

The antibody generated from these peptides can be polyclonal or monoclonal depending upon the particular application for which it is designed and/or the variability of the protein near the epitope. As aforesaid, these antibodies can be prepared by techniques well known to the skilled artisan. For example, the desired fragment of the protein or chemically synthesized peptide can be conjugated to keyhole limpet hemocyanin (KLH) and used to raise an antibody in an animal such as a rabbit. Typically, the peptide-KLH conjugate is injected several times over a period of about two months to generate antibodies. Antibodies are then collected from serum by standard techniques. Alternatively, monoclonal antibodies can be produced in cells which produce antibodies to the peptide by using standard fusion techniques for forming hybridoma cells. [Kohler, G., et al., (1975) *Nature* 256:495 which is incorporated by reference.] Typically, this involves fusing an antibody producing cell with an immortal cell line such as a myeloma cell to produce the hybrid cell. In another method, monoclonal antibodies can be produced from cells by the method of Huse, et al., (1989) *Science* 246:1275 which is incorporated herein by reference.

In one example, hybridomas can be generated by immunization of mice with one of the immunogenic peptides. The mice can be immunized intraperitoneally (i.p.) with a sufficient amount of peptide. This can then be followed immediately by an i.p. injection of, for example, cyclophosphamide in $H_2O$. The cyclophosphamide treatment is repeated one and two days following the primary injection. About two weeks following immunization, mice are again injected with a sufficient amount of the peptide and then allowed to rest for another two weeks. Four days following the second injection, the animals are sacrificed and their spleens obtained for the first fusion.

Hybridomas are produced by fusing cells by typical techniques, such as from immunized mice with SP2/O myeloma cells by a polyethylene glycol (PEG) method. Cells are aseptically removed from immunized mice and a single cell suspension of the spleen cells obtained by perfusing the spleen with serum-free media (e.g., DME). Spleen cells and myeloma cells are mixed together at a ratio, for example, 5 to 1, spleen cells to myeloma cells. The cells are then centrifuged and the supernatant removed by aspiration. The cells are then grown in medium by standard techniques. Hybridomas, which grow after the fusion procedure, are then screened for secretion of antibodies specific to the $\beta_5$ epitopes by an ELISA assay on a cell lysate. Hybridomas, that produce positive results, are expanded and cloned by limiting dilution to assure that the cells and resulting antibodies are indeed, monoclonal. Hybridoma colonies that test positive for the presence of antibody to one of the desired $\beta_5$ epitopes are diluted in media to a concentration of, for example, 5 hybridoma cells per mililiter. Once colonies grow, the supernatants are again tested for the presence of antibody to the $\beta_5$ epitope. If the results are positive when tested by ELISA assay, the colonies are cloned again by limiting dilution.

In accordance with this invention, an antibody or cocktail of antibodies can be used for detection. These antibodies can be labeled directly with a reporter or indirectly with a member of a specific binding pair using conventional techniques.

Specific binding pairs can be of the immune or non-immune type. Immune specific binding pairs are exemplified by antigen-antibody systems of hapten/anti-hapten systems. There can be mentioned fluorescein/anti-fluorescein, dinitrophenyl/anti-dinitrophenyl, biotin/anti-biotin, peptide/anti-peptide and the like. The antibody member of the specific binding pair can be produced by customary methods familiar to those skilled in the art. Such methods involve immunizing an animal with the antigen member of the specific binding pair. If the antigen member of the specific binding pair is not immunogenic, e.g., a hapten, it can covalently coupled to a carrier protein to render it immunogenic.

Non-immune binding pairs include systems wherein the two components share a natural affinity for each other but are not antibodies. Exemplary non-immune pairs are biotin-streptavidin, intrinsic factor-vitamin $B_{12}$, folic acid-folate binding protein and the like.

A variety of methods are available to covalently label antibodies with members of specific binding pairs. Methods are selected based upon the nature of the member of the specific binding pair, the type of linkage desired, and the tolerance of the antibody to various conjugation chemistries. Biotin can be covalently coupled to antibodies by utilizing commercially available active derivatives. Some of these are biotin-N-hydroxy-succinimide which binds to amine groups on proteins; biotin hydrazide which binds to carbohydrate moieties, aldehydes and carboxyl groups via a carbodiimide coupling; and biotin maleimide and iodoacetyl biotin which bind to sulfhydryl groups. Fluorescein can be coupled to protein amine groups using fluorescein isothiocyanate. Dinitrophenyl groups can be coupled to protein amine groups using 2,4-dinitrobenzene sulfate or 2,4-dinitrofluorobenzene. Other standard methods of conjugation can be employed to couple monoclonal antibodies to a member of a specific binding pair including dialdehyde, carbodiimide coupling, homofunctional crosslinking, and heterobifunctional crosslinking. Carbodiimide coupling is an effective method of coupling carboxyl groups on one substance to amine groups of another. Carbodiimide coupling is facilitated by using the commercially available reagent 1-ethyl-3-(dimethyl-aminopropyl)-carbodiimide (EDAC).

Homobifunctional crosslinkers, including the bifunctional imidoesters and bifunctional N-hydroxy-succinimide esters, are commercially available and are employed for coupling amine groups on one substance to amine groups on another. Heterobifunctional crosslinkers are reagents which possess different functional groups. The most common commercially available heterobifunctional crosslinkers have an amine reactive N-hydroxysuccinimide ester as one functional group, and a sulfhydryl reactive group as the second functional group. The most common sulfhydryl reactive groups are maleimides, pyridyl disulfides and active halogens. One of the functional groups can be a photoactive aryl nitrene, which upon irradiation reacts with a variety of groups.

The detectably-labeled antibody, detectably-labeled antibodies, or detectably-labeled member of the specific binding pair is coupled to a reporter which can be a radioactive isotope, enzyme, fluorogenic, chemiluminescent or electrochemical materials. Two commonly used radioactive isotopes are $^{125}I$ and $^3H$. Standard radioactive isotopic labeling procedures include the chloramine T, lactoperoxidase and Bolton-Hunter methods for $^{125}I$ and reduction methylation for $^3H$.

Enzymes suitable for use in this invention include, but are not limited to, horseradish peroxidase, alkaline phosphatase, β-galactosidase, glucose oxidase, luciferase, β-lactamase, urease and lysozyme. Enzyme labeling is facilitated by using dialdehyde, carbodiimide coupling, homobifunctional crosslinkers and heterobifunctional crosslinkers as described above for coupling an antibody with a member of a specific binding pair.

The labeling method chosen depends on the functional groups available on the enzyme and the material to be labeled, and the tolerance of both to the conjugation conditions. The labeling method used in the present invention can be one of, but not limited to, any conventional methods currently employed including those described by Engvall and Pearlmann, (1971) *Immunochemistry*, 8:871; Avrameas and Ternynck (1975) *Immunochemistry*, 8:1175; Ishikawa, et al., (1983) *J. Immunoassay*, 4(3):209–327; and Jablonski, (1985) *Anal. Biochem.*, 148–199.

Labeling can be accomplished by indirect methods such as using spacers or other members of specific binding pairs. An example of this is the detection of a biotinylated antibody with unlabeled streptavidin and biotinylated enzyme, with streptavidin and biotinylated enzyme being added either sequentially or simultaneously. Thus, according to the present invention, the antibody used to detect can be detectably-labeled directly with a reporter or indirectly with a first member of a specific binding pair. When the antibody is coupled to a first member of a specific binding pair, then detection is effected by reacting the antibody-first member of a specific binding complex with the second member of the binding pair which is labeled or unlabeled as mentioned above.

Moreover, the unlabeled detector antibody can be detected by reacting with the unlabeled antibody with a labeled antibody specific for the unlabeled antibody. Such an anti-antibody can be labeled directly or indirectly using any of the approaches discussed above. For example, the anti-antibody can be coupled to biotin which is detected by reacting with the streptavidine-horseradish peroxidase system discussed above.

One of the preferred embodiments of this invention utilizes biotin. The biotinylated antibody is in turn reacted with streptavidin-horeradish peroxidase complex. Orthophenylenediamine, 4-chloro-naphthol, or tetramethylbenzidine (TMB) can be used to effect chromogenic detection.

The preferred immunoassay format for practicing this invention is a forward sandwich assay in which the capture reagent has been immobilized, using conventional techniques, on the surface of the support.

Suitable supports used in assays include synthetic polymer supports, such as polypropylene, polystyrene, substituted polystyrene, e.g., aminated or carboxylated polystyrene; polyacrylamides; polyamides; polyvinylchloride, etc.; glass beads; agarose; nitrocellulose, etc.

In another embodiment, the $\beta_5$ nucleotide sequence of the present invention is used as a probe to identify and quantify $\beta_5$ RNA, preferably mRNA, present in a test sample. The test sample may be either tissue or biological fluid. The total RNA from a test sample is isolated, using standard procedures, and affixed to a support such a nitrocellulose. Preferably, the total RNA can be separated by electrophoresis in a 1% agarose gel containing formaldehyde, and then blotted onto nitrocellulose. The $\beta_5$ probe can be labeled with a radionucleotide, preferably $^{32}P$, or a biotinylated nucleotide using standard techniques. The affixed RNA can then be screened with the labeled $\beta_5$ nucleotide sequence probe, either DNA or RNA probes, preferably a DNA probe, or a fragment thereof by contacting the $\beta_5$ probe with the RNA sample to assayed using standard techniques and conditions. The filter is washed to remove unbound probe, using standard methods, and the probe remaining bound to the sample is measured, for example, using autoradiography if the probe is radioactive, or streptavidin-horseradish peroxidase complex if the probe is biotinylated. Binding of the labeled probe to the test RNA sample is indicative of the presence of the $\beta_5$ subunit protein and can confirm predictions that the test sample contains a carcinoma.

In a further embodiment, oligonucleotide primers can be produced from any region of the $\beta_5$ nucleotide sequence of the present invention, and used in the polymerase change reaction (PCR), as discussed, for example in U.S. Pat. No. 4,683,195, to detect the presence or absence of the $\beta_5$ nucleotide sequence, either DNA or RNA, in a test sample.

These examples discussed below are intended to illustrate the invention and should not be construed as limitations.

EXAMPLES

EXAMPLE I

Isolation of cDNA Encoding the $\beta_5$ Gene

Two oligonucleotides, a 32-fold degenerate 23mer and a 16-fold degenerate 21mer, were synthesized based on $\beta_1$, $\beta_2$, and $\beta_3$ subunit sequences from a highly conserved region (FIG. 1). Two overlapping oligonucleotides were made from the cDNA region most highly conserved among $\beta_1$, $\beta_2$ and $\beta_3$ subunits, which is the region coding for the amino acid sequence DLYYLMDLSYSM (SEQ ID NO:3). These oligonucleotides were then used as probes for screening duplicate filters of a λgt11 cDNA library made from thymic epithelial cells (Clonetech Laboratories, Inc.) A third filter was probed with an insert corresponding to the 3' half of the $\beta_1$ gene [base pairs 1133–3614 (Argraves, et al., (1987) *J. Cell Biol.*, supra)]. Phage clones that hybridized with both oligonucleotides, but not with a partial $\beta_1$ cDNA probe, were selected and further purified. Initial screening of 1.8×10⁵ λgt11 recombinant phage plaques yielded six clones. Partial sequencing revealed that four of these clones had sequences identical to the integrin $\beta_2$ subunit, and one of them was identical to the integrin $\beta_2$ subunit, and one of them was identical to the N-terminal portion of the integrin $\beta_1$ sequence. A single clone of 3.0 kb size, designated clone 9.2, was found to be distinct from $\beta_1$, $\beta_2$ and $\beta_3$. As shown in FIG. 1, this new clone matched oligonucleotide probe 1 in 23/23 positions and matched probe 2 in 18/21 positions.

Clone 9.2, containing a 3.0 kb $\beta_5$ insert, was used for secondary screening and eight additional phage plaques were selected, and those $\beta_5$ inserts were subcloned into the bluescript vector (Stratagene Co.).

DNA Sequencing

Clones with $\beta_5$ cDNA inserts were sequenced on both strands by the dideoxy sequencing method. After sequencing the ends of the available $\beta_5$ clones (FIG. 3), sequencing of the remaining gaps was facilitated by using synthetic primers of 15–17 bp prepared from known $\beta_5$ sequence.

Northern Blotting

To obtain information regarding the message corresponding to clone 9.2, RNA from PEER (a T lymphoblastoid cell line), CCL 228 (a colon carcinoma cell line) and thymocytes was analyzed in a hybridization experiment (FIG. 2). Total RNA (10 µg/lane) from CCL 228 cells, PEER cells and thymocytes was separated by electrophoresis in a 1% agarose gel containing formaldehyde, and then after blotting onto nitrocellulose, the RNA was probed with a $^{32}P$-labeled SphI fragment derived from clone 9.2. A single band of 3.5 kb was observed in the lane containing RNA from CCL 228 cells, but was absent from thymocytes and PEER cells. Probing of the same blot with a control probe revealed that similar amounts of RNA were present in all three lanes (not shown). The results in FIG. 2 confirmed that clone 9.2 was distinct from $\beta_1$ and $\beta_2$ for which messages are present in PEER cells and thymocytes, and also showed that clone 9.2 was distinct from $\beta_4$ which hybridizes with a 6–7 kb message from CCL 228 cells (C. Crouse and M. Hemler, unpublished).

Human $\beta_5$ cDNA Sequence

Because the new $\beta$ clone differed in sequence and/or message size from $\beta_1$, $\beta_2$, $\beta_3$ or $\beta_4$, it was designated $\beta_5$. The $\beta_5$ clone 9.2 appeared to be incomplete, so it was used as a probe for further screening of the λgt11 thymic epithelial library. Eight additional $\beta_5$ clones were obtained, including one which spanned the entire $\beta_5$ clones were obtained, including one which spanned the entire $\beta_5$ coding region (FIG. 3). The complete $\beta_5$ sequence was determined in both directions from these clones, with the help of 13 oligonucleotide primers (15–17 bp each), synthesized at ~200 bp intervals. The complete sequence of the coding region, as well as 3' and 5' untranslated regions, is presented in FIG. 4. (SEQ ID NO:1)

The GLNICT sequence (SEQ ID NO:4) in clone 5.1 is likely to be the N-terminus of the $\beta_5$ protein because it closely matched the GPNICT (SEQ ID NO:7) sequence at the N-terminus of $\beta_3$. Consistent with this assumption, direct N-terminal amino acid sequencing yielded a XLNICT (SEQ ID NO:5) sequence for $\beta_x$ (D. Cheresh, personal communication), which may be related to or identical to $\beta_5$. However, the function and structure of $\beta_x$ has yet been fully elucidated. Further, as discussed below, we have found that not all $\alpha^V$ is associated with $\beta_5$. The 5' untranslated region in clone 5.1 (337 nucleotides) ends with a consensus CCACC sequence characteristic of a translational start site (Kozak, (1987) *Nucleic Acids Res.*, 15:8125–8132). Following the predicted methionine initiation codon, there is an open reading frame of 2397 nucleotides corresponding to 799 amino acids. The 23 amino acids preceding the N-terminus are rich in hydrophobic residues as expected for a signal sequence (von Heijne, (1984) *J. Mol. Biol.*, 173:243–251), and are followed by 776/773 amino acids making up the mature protein. Another region of 23 hydrophobic amino acid residues (amino acids 697–719) corresponds to the transmembrane region. Between amino acids 438–592, $\beta_5$ contains four cysteine-rich motifs, each with eight cysteines in the pattern of CxCyyyCyyyCyyyCxCxxCxC, where x represent one amino acid and yyyy represents a stretch of 7–13 amino acids. CxCxxCxC forms the core of the motif, although the first core cysteine residue is absent in the first repeat. The $\beta_5$ sequence reveals eight potential N-glycosylation sites (Asn-X-Ser/Thr), not counting two such sites in the cytoplasmic domain of the molecule. At least six of these glycosylation sites (averaged 2500 $M_r$) may be utilized because the 86,000 $M_r$ predicted size of $\beta_5$ (derived from the amino acid sequence of the mature protein) is 15,000 $M_r$ less than the 100,000 $M_r$ size estimated by SDS-PAGE (see FIG. 6).

TABLE I

| Clone description | Amino Acid Variations Among β5 Clones |  |  |  |
|---|---|---|---|---|
| | Amino acid positions | | | |
| | 336–338 | 379–381 | 708 | 767–769 (FNK) |
| 3Q | — | — | G | present |
| 9J | — | — | I | absent |
| 6O | — | — | I | absent |
| 2M | — | K D E | I | absent |
| 1C | G I R | Q D G | I | absent |
| 4H | I L D | Q D G | I | present |
| 9.2 | I L D | Q D G | I | absent |
| 8E | I L D | Q D G | — | — |
| 5.1 | I L D | Q D G | I | present |

Sequences differing from the prototype clone (5.1) are represented in bold letters. Dashes indicate sequences not determined because the clone does not span the corresponding region.

Clonal Heterogeneity

Sequencing information from the eight available clones indicated that there were four sites where one or more of the clones differed from each other. These changes each involved multiples of three nucleotides thus resulting in changes in amino acid sequences (Table I). For example, at position 336–338, clone 1C expressed a Gly-Ile-Arg sequence, whereas fourothers had an Ile-Leu-Asp. Similarly, at position 379–381, five different clones expressed Gln-Asp-Gly, whereas clone 2M expressed Lys-Asp-Glu, and at position 708, all clones expressed in isoleucine, except clone 3Q, which had a glycine. In the cytoplasmic domain, immediately after the Phe-Asn-Lys sequence at position 764–766, a second Phe-Asn-Lys sequence was present in clones 3Q, 4H and 5.1 (amino acids 767–769), but not in five other clones. Thus far, clones 4H, 9.2 and 5.1 differ only in their Phe-Asn-Lys sequences, and otherwise appear to define prototype $\beta_5$ clones.

Comparison with Other Human β Subunits

When compared with the other integrin β subunits that have been sequenced (FIG. 5), $\beta_5$ was most related to $\beta_3$ (54.9% identify), and less similar to $\beta_1$ (43.1%) or $\beta_2$ (37.6%). All 56 cysteines present in the coding region of $\beta_5$ are conserved among each of the other β subunits, including the cysteine-rich domain. In the cytoplasmic domain of $\beta_5$, which is 10 amino acids longer than the other β subunit cytoplasmic domains (FIG. 5), there are two sites potentially meeting the requirements for tyrosine kinase phosphorylation sites (Hunter and Cooper, (1985) *Annu. Rev. Biochem.*, 54:897–930). The site near the tyrosine at position 751 is conserved in the $\beta_1$ and $\beta_3$ sequences, and resembles the EGF receptor tyrosine kinase site as noted previously (Tamkun, et al., (1986) *Cell*, supra). Notably, the tyrosine at position 743 in $\beta_5$, which also satisfies the requirements for a tyrosine kinase site, is not conserved in other β subunits.

Production of Antibodies and Immunoprecipitation

The peptide (CTHTVDFTFNKFNKSYNGTVD) (SEQ ID NO:6) was prepared by Multiple Peptide Systems (CA) and, except for the N-terminal cysteine, corresponds to the predicted 20 amino acids at the C-terminus of the $\beta_5$ cDNA sequence (FIG. 4). Note that two repeating FNK sequences are present in the peptide, although several clones only had a single FNK sequence (Table I). The peptide was coupled to keyhole limpet hemocyanin (KLH) using m-maleimido-benzoyl-N-hydroxysulfosuccinimide ester (Pierce Chemical Co.) through the N-terminal cysteine residue as previously described (Kitagawa and Aikawa, (1976) *J. Biochem.*, 79:233–236). The KLH-conjugated peptide was used to immunize rabbits, and after 3–4 injections at 2 week intervals, the resulting rabbit antiserum was of suitable titer for use in immunoprecipitation experiments.

Immunoprecipitation of integrin subunits from extracts of $^{125}$I-surface-labeled cells were carried out as previously described (Hemler, et al., (1987) *J. Biol. Chem.*, 262:3300–3309). MAbs used for immunoprecipitation in this study include the anti-$\beta_1$ mAb A-1A5 (Hemler, et al., (1984) *J. Immunol.*, 132:3011–3018), anti-$\beta_1$ mAb TSI/18 (Sanchez-Madrid, et al., (1983) *J. Exp. Med.*, 158:1785–1803), anti-$\beta_3$ mAb AP-5 (from Dr. T. Kunicki) anti-$\beta_3$ mAb Ab-15 (from Dr. M. Ginsberg), anti-$\beta_4$ mAb 439-9B (Kennel, et al., (1989) *J. Biol. Chem.*, 264-15515-1521) and the anti-$\alpha^v$ mAb LM142 (Cheresh and Harper, (1987) *J. Biol. Chem.*, 262:1434–1437).

Identification of $\beta_5$ and its Associated $\alpha$ Subunit

An antiserum raised against a synthetic peptide corresponding to the $\beta_5$ cytoplasmic domain (residues 757–776), discussed above, was employed in immunoprecipitation experiments to analyze the $\beta_5$ protein and any associated $\alpha$ subunits. As shown (FIG. 6A, lane d) the anti-$\beta_5$ antiserum yielded a pattern of two protein bands (165,000 and 95,000$M_r$) from surface-labeled CCL 228 cells. This pattern was clearly distinct from the $\beta_1$ precipitation (lane a), and the blank $\beta_2$ and $\beta_3$ precipitations (lanes b and c). Because the integrin $\alpha^v$ subunit migrates at 165,000$M_r$, and is known to be present on carcinoma cells in association with a novel $\beta$ subunit (Cheresh, et al., (1989) *Cell*, supra), an anti-$\alpha^v$ immunoprecipitation was carried out for comparison. As shown, the anti-$\alpha^v$ monoclonal antibody (LM142) yielded a pattern of bands (lane e) with mobilities that closely resembled those seen in the anti-$\beta_5$ immunoprecipitation (lane d).

To better demonstrate the identify of the $\alpha$ subunit associating with $\beta_5$, immunodepletion experiments were carried out. When extract from surface-labeled CCL 228 cells was depleted of all $\alpha^v$-reactive material (FIG. 6B, lane l), all $\beta_5$-reactive material was removed at the same time (lane k). Conversely, when all $\beta_5$-reactive material was depleted (FIG. 6B, lane i) most, but not all of the 165,000 $M_r$ protein recognized by LM142 was also removed. In undepleted extract (lanes g and h), substantial amounts of material were precipitated by the anti-$\beta_5$ and anti-$\alpha^v$ reagents. Together these results suggest that (i) all of the $\beta_5$ on CCL 228 cells is associated with the $\alpha^v$ subunit and (ii) a small proportion of $\alpha^v$ is not associated with the $\beta_5$ subunit (as defined using the anti-$\beta_5$ peptide antiserum), and thus perhaps could be associated with some other $\beta$ subunit, for example $\beta_x$.

In another experiment, the mobilities of $\beta_5$ and $\beta_3$ were compared when immunoprecipitated from the same cell line (J82 bladder carcinoma cells). As shown (FIG. 6C), the $\beta_5$ protein (lane n) had a slightly larger apparent size than $\beta_3$ (lane m). In the same experiment, the mobility of $\alpha^v$ was identical whether co-precipitated with $\beta_3$ or $\beta_5$ or precipitated directly (compare lanes m, n and o).

The substantial increase in the apparent size of $\beta_5$ upon reduction (FIG. 6D, lane q) compared to non-reduced conditions (lane p) is characteristic of other integrin $\beta$ subunits. Also upon reduction, the $\alpha_v$ subunit migrated faster due to the cleavage of a 25,000 $M_r$ disulfide-linked C-terminal fragment, as previously described (Suzuki, et al., (1986) *Proc. Natl. Acad. Sci. USA*, 83:8614–8618).

Distribution of $\beta_5$

The distribution of $\beta_5$ on various cell types was studied by immunoprecipitation of surface $^{125}$-labeled cells. The $\beta_5$ subunit was most prevalent on various types of carcinoma cells. It was also present on cell lines of hepatoma and fibroblast origin, but was absent on lymphocytes and platelets (Table II). On some of the cell lines (CCL 228, A431, GepG2) $\beta_5$, but not $\beta_3$, was present in association with $\alpha^v$, whereas on other cell lines (PHEC, JY), $\beta_3$ but not $\beta_5$ was present with $\alpha^v$. On the J82 cell line, and perhaps also the MRC-5 fibroblast cells, both $\beta_5$ and $\beta_3$ were present in association with $\alpha^v$. Platelets and the T cell line PEER lacked detectable levels of either $\alpha^v$ or $\beta_5$. The $\beta_4$ subunit, like $\beta_5$, was expressed on carcinoma cell lines and absent from platelets and lymphoid cells. Also, as expected, $\beta_1$ was present on all of the cell lines, and $\beta_2$ was only expressed on the lymphoid cell lines.

EXAMPLE II

Detection of $\beta_5$ in Biological Samples

Polystyrene plates (Nunc) are coated with either 20 microgram per millileter (μg/ml) of an anti-$\beta_5$ monoclonal antibody (Mab), a combination of anti-$\beta_5$ Mabs, or a polyclonal antibody for the purpose of capturing $\beta_5$ protein from various biological specimens. Mabs are diluted in 0.1M carbonate buffer (pH 9.6) and 100 microliters (μl) added to

TABLE II

| | | Distribution of $\alpha^v$, $\beta_5$ and other integrin $\beta$ subunits | | | | | |
|---|---|---|---|---|---|---|---|
| Name | Cell Type | $\beta_1$ | $\beta_2$ | $\beta_3$ | $\beta_4$ | $\beta_5$ | $\alpha^v$ |
| CCL228 | colon carcinoma | ++ | − | − | ++ | + | + |
| A431 | epidermoid carcinoma | +++ | − | − | ++ | +/− | + |
| J82 | bladder carcinoma | +++ | − | + | +/− | + | ++ |
| HepG2 | hepatoma | +++ | − | − | + | + | + |
| MRC-5 | fibroblast | +++ | − | +/− | ND | + | + |
| PHEC | endothelial | ++ | − | + | +/− | − | + |
| JY | B cell | − | + | + | ND | − | + |
| PEER | T cell | ++ | ++ | − | − | − | − |
| Platelet | | ++ | − | +++ | − | − | − |

Distribution of $\beta$ and $\alpha^v$ subunits was determined by immuno-precipitation.
Distribution of $\beta_4$ on PEER cells. PHEC and platelets was reported elsewhere (Hemler, et al., (1989) J. Biol. Chem., supra). Expression of $\beta_4$ on JY and MRC-5 cells was not determined, but other B call and fibroblast cell lines were negative (not shown).

each well of the microtiter plate. The plates are then incubated overnight at 4° C.

After incubation, the coating material is decanted from the plates and 250 μl of blocking buffer (PBS with 2% bovine serum albumin (BSA), 10% β-lactose and 0.01% thimersal) was added to each well. The blocking buffer is decanted and 250 μl of fresh blocking buffer added to each well in order to block sites on the microtiter wells not coated with the anti-$β_5$ antibody. Plates are incubated for 2 hours at room temperature. The blocking buffer is decanted and plates blotted with paper towels. Plates are dried overnight in a hood at room temperature and then stored covered at 4° C. until use.

Specimens to be evaluated for the $β_5$ protein consist of lysates prepared from normal, preneoplastic or neoplastic cells or human body fluids such as serum, plasma or urine. The specimen is then added to the antibody coated wells in order to capture the $β_5$ protein from the specimen. The plates are incubated overnight at room temperature. After incubation, the plates are washed six times with DuPont Plate Wash Buffer (PBS, 0.05%, TWEEN20, polyoxyethylene (20) sorbitan monolaurate and a Dynatech Plate Washer in order to remove unbound biological specimen.

Another anti-human $β_5$ Mab coupled to biotin is added to each well and incubated for 30 minutes at room temperature. Plates were then washed six times with DuPont Plate Wash Buffer. To detect the biotinylated anti-$β_5$ Mab, streptavidin-horseradish peroxidase is added at a 1:2500 dilution and allowed to incubate for 15 minutes at room temperature. Plates are then washed six times with DuPont Plate Wash Buffer. To complete the reaction, the substrate orthophenylenediamine (OPD) is added for 1 hour at room temperature. The reaction is stopped with sulfuric acid and the optical density is determined using a Molecular Devices Plate Reader at a wavelength of 490 nm.

---

What is claimed is:

1. A method of detecting or quantifying the presence of $\beta_5$ in a human biological specimen, which comprises:
   (a) contacting the biological specimen with at least one antibody probe which is capable of specifically binding $\beta_5$; and
   (b) detecting the presence of $\beta_5$ by determining whether binding has occurred.

2. The method of claim 1, wherein the biological specimen is a biological fluid or a tissue sample.

3. The method according to claim 1, wherein the antibody probe is selected from the group consisting of monoclonal and polyclonal antibodies.

4. The method according to claim 1, wherein the biological fluid is selected from the group consisting of blood, serum, plasma, urine, cerebrospinal fluid, supernatant from normal cell lysate, supernatant from preneoplastic cell lysate, supernatant from neoplastic cell lysate, and breast aspirates.

5. An immunoassay for detecting the presence of $\beta_5$ in a human biological specimen which comprises:
   (a) reacting the specimen with at least one first monoclonal antibody which is capable of specifically binding to $\beta_5$;
   (b) reacting the product of step (a) with at least one detectably-labeled second monoclonal antibody which is capable of specifically binding to $\beta_5$ at an epitope different from the epitope bound by the first antibody; and
   (c) detecting the presence of $\beta_5$ by detecting the product of step (b).

6. An assay according to claim 5, wherein immunoreactive fragments of the antibodies which bind the same epitope are used.

7. An assay according to claim 5, wherein the detectable-label is selected from the group consisting of radioisotopes, enzymes, fluorogenic, chemiluminescent, and electrochemical materials.

8. An assay according to claim 5, wherein the second antibody is conjugated to biotin.

9. An assay according to claim 5, wherein the biotin-conjugated antibody is detected by reacting the biotinylated complex first with streptavidin-horseradish peroxidase followed by reaction orthophenylenediamine.

10. A method of detecting the presence of $\beta_5$ mRNA in a biological specimen which comprises;
    (a) contacting the biological specimen with a nucleotide probe to $\beta_5$ mRNA under conditions suitable for selectively detecting the mRNA, said probe being capable of hybridizing to the DNA sequence of SEQ ID NO:1; and
    (b) detecting the presence of $\beta_5$ mRNA by determining whether binding has occurred.

11. A DNA of SEQ ID. NO:1 in isolated and purified form.

12. An isolated DNA sequence encoding the amino acid sequence of SEQ ID NO:2.

13. An isolated DNA sequence having the nucleotide sequence represented in SEQ ID NO:1.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 3415 base pairs
        ( B ) TYPE: nucleic acid
        ( C ) STRANDEDNESS: single
        ( D ) TOPOLOGY: linear ( i x ) FEATURE:
        ( A ) NAME/KEY: mat peptide
        ( B ) LOCATION: 406..2733

( i x ) FEATURE:
        ( A ) NAME/KEY: CDS
        ( B ) LOCATION: 337..2733

( x i ) SEQUENCE DESCRIPTION: SEQ ID NO:1:

```
GCCGCCGAGG  GCAGCCAGCC  CCTCCCCTAC  CCGGAGCAGC  CCGCTGGGGC  CGTCCCGAGC         60

GGCGACACAC  TAGGAGTCCC  GGCCGGCCAG  CCAGGGCAGC  CGCGGTCCCG  GGACTCGGCC        120

GTGAGTGCTG  CGGGACGGAT  GGTGGCGGCG  GGAGCGCGGA  GACCACGGCG  GGCGCCGTGG        180

AGCCGGGCGC  CGTGCAGCCG  GAGCTGCGCG  CGGGGCATGC  GGCTGCGCCC  CGGCCCCTCG        240

GCCCCCGGCC  TCGGCCCCCG  CGCTCCGGCC  CCAGCCCCGG  CCGCCGGCCC  CCGCGGAGTG        300

CAGCGACCGC  GCCGCCGCTG  AGGGAGGCGC  CCCACC ATG  CCG  CGG  GCC  CCG  GCG        354
                                           Met  Pro  Arg  Ala  Pro  Ala
                                           -23            -20

CCG  CTG  TAC  GCC  TGC  CTC  CTG  GGG  CTC  TGC  GCG  CTC  CTG  CCC  CGG  CTC   402
Pro  Leu  Tyr  Ala  Cys  Leu  Leu  Gly  Leu  Cys  Ala  Leu  Leu  Pro  Arg  Leu
          -15                    -10                      -5

GCA  GGT  CTC  AAC  ATA  TGC  ACT  AGT  GGA  AGT  GCC  ACC  TCA  TGT  GAA  GAA   450
Ala  Gly  Leu  Asn  Ile  Cys  Thr  Ser  Gly  Ser  Ala  Thr  Ser  Cys  Glu  Glu
     1                    5                    10                      15

TGT  CTG  CTA  ATC  CAC  CCA  AAA  TGT  GCC  TGG  TGC  TCC  AAA  GAG  GAC  TTC   498
Cys  Leu  Leu  Ile  His  Pro  Lys  Cys  Ala  Trp  Cys  Ser  Lys  Glu  Asp  Phe
               20                        25                       30

GGA  AGC  CCA  CGG  TCC  ATC  ACC  TCT  CGG  TGT  GAT  CTG  AGG  GCA  AAC  CTT   546
Gly  Ser  Pro  Arg  Ser  Ile  Thr  Ser  Arg  Cys  Asp  Leu  Arg  Ala  Asn  Leu
              35                        40                       45

GTC  AAA  AAT  GGC  TGT  GGA  GGT  GAG  ATA  GAG  AGC  CCA  GCC  AGC  AGC  TTC   594
```

|  |  |  |  |  |  |  |  |  |  |  |  |  |  |  |  |
|---|---|---|---|---|---|---|---|---|---|---|---|---|---|---|---|
| Val | Lys | Asn | Gly | Cys | Gly | Gly | Glu | Ile | Glu | Ser | Pro | Ala | Ser | Ser | Phe |
|  |  | 50 |  |  |  | 55 |  |  |  |  | 60 |  |  |  |  |

```
CAT GTC CTG AGG AGC CTG CCC CTC AGC AGC AAG GGT TCG GGC TCT GCA    642
His Val Leu Arg Ser Leu Pro Leu Ser Ser Lys Gly Ser Gly Ser Ala
    65                  70                  75

GGC TGG GAC GTC ATT CAG ATG ACA CCA CAG GAG ATT GCC GTG AAC CTC    690
Gly Trp Asp Val Ile Gln Met Thr Pro Gln Glu Ile Ala Val Asn Leu
80                  85                  90                      95

CGG CCC GGT GAC AAG ACC ACC TTC CAG CTA CAG GTT CGC CAG GTG GAG    738
Arg Pro Gly Asp Lys Thr Thr Phe Gln Leu Gln Val Arg Gln Val Glu
                100                 105                 110

GAC TAT CCT GTG GAC CTG TAC TAC CTG ATG GAC CTC TCC CTG TCC ATG    786
Asp Tyr Pro Val Asp Leu Tyr Tyr Leu Met Asp Leu Ser Leu Ser Met
            115                 120                 125

AAG GAT GAC TTG GAC AAT ATC CGG AGC CTG GGC ACC AAA CTC GCG GAG    834
Lys Asp Asp Leu Asp Asn Ile Arg Ser Leu Gly Thr Lys Leu Ala Glu
        130                 135                 140

GAG ATG AGG AAG CTC ACC AGC AAC TTC CGG TTG GGA TTT GGG TCT TTT    882
Glu Met Arg Lys Leu Thr Ser Asn Phe Arg Leu Gly Phe Gly Ser Phe
    145                 150                 155

GTT GAT AAG GAC ATC TCT CCT TTC TCC TAC ACG GCA CCG AGG TAC CAG    930
Val Asp Lys Asp Ile Ser Pro Phe Ser Tyr Thr Ala Pro Arg Tyr Gln
160                 165                 170                 175

ACC AAT CCG TGC ATT GGT TAC AAG TTG TTT CCA AAT TGC GTC CCC TCC    978
Thr Asn Pro Cys Ile Gly Tyr Lys Leu Phe Pro Asn Cys Val Pro Ser
                180                 185                 190

TTT GGG TTC CGC CAT CTG CTG CCT CTC ACA GAC AGA GTG GAC AGC TTC   1026
Phe Gly Phe Arg His Leu Leu Pro Leu Thr Asp Arg Val Asp Ser Phe
            195                 200                 205

AAT GAG GAA GTT CGG AAA CAG AGG GTG TCC CGG AAC CGA GAT GCC CCT   1074
Asn Glu Glu Val Arg Lys Gln Arg Val Ser Arg Asn Arg Asp Ala Pro
        210                 215                 220

GAG GGG GGC TTT GAT GCA GTA CTC CAG GCA GCC GTC TGC AAG GAG AAG   1122
Glu Gly Gly Phe Asp Ala Val Leu Gln Ala Ala Val Cys Lys Glu Lys
    225                 230                 235

ATT GGC TGG CGA AAG GAT GCA CTG CAT TTG CTG GTG TTC ACA ACA GAT   1170
Ile Gly Trp Arg Lys Asp Ala Leu His Leu Leu Val Phe Thr Thr Asp
240                 245                 250                 255

GAT GTG CCC CAC ATC GCA TTG GAT GGA AAA TTG GGA GGC CTG GTG CAG   1218
Asp Val Pro His Ile Ala Leu Asp Gly Lys Leu Gly Gly Leu Val Gln
                260                 265                 270

CCA CAC GAT GGC CAG TGC CAC CTG AAC GAG GCC AAC GAG TAC ACA GCA   1266
Pro His Asp Gly Gln Cys His Leu Asn Glu Ala Asn Glu Tyr Thr Ala
            275                 280                 285

TCC AAC CAG ATG GAC TAT CCA TCC CTT GCC TTG CTT GGA GAG AAA TTG   1314
Ser Asn Gln Met Asp Tyr Pro Ser Leu Ala Leu Leu Gly Glu Lys Leu
        290                 295                 300

GCA GAG AAC AAC ATC AAC CTC ATC TTT GCA GTG ACA AAA AAC CAT TAT   1362
Ala Glu Asn Asn Ile Asn Leu Ile Phe Ala Val Thr Lys Asn His Tyr
    305                 310                 315

ATG CTG TAC AAG AAT TTT ACA GCC CTG ATA CCT GGA ACA ACG GTG GAG   1410
Met Leu Tyr Lys Asn Phe Thr Ala Leu Ile Pro Gly Thr Thr Val Glu
320                 325                 330                 335

ATT TTA GAT GGA GAC TCC AAA AAT ATT ATT CAA CTG ATT ATT AAT GCA   1458
Ile Leu Asp Gly Asp Ser Lys Asn Ile Ile Gln Leu Ile Ile Asn Ala
                340                 345                 350

TAC AAT AGT ATC CGG TCT AAA GTG GAG TTG TCA GTC TGG GAT CAG CCT   1506
Tyr Asn Ser Ile Arg Ser Lys Val Glu Leu Ser Val Trp Asp Gln Pro
            355                 360                 365

GAG GAT CTT AAT CTC TTC TTT ACT GCT ACC TGC CAA GAT GGG GTA TCC   1554
```

```
           Glu  Asp  Leu  Asn  Leu  Phe  Phe  Thr  Ala  Thr  Cys  Gln  Asp  Gly  Val  Ser
                     370                      375                     380

TAT  CCT  GGT  CAG  AGG  AAG  TGT  GAG  GGT  CTG  AAG  ATT  GGG  GAC  ACG  GCA                1602
Tyr  Pro  Gly  Gln  Arg  Lys  Cys  Glu  Gly  Leu  Lys  Ile  Gly  Asp  Thr  Ala
     385                      390                     395

TCT  TTT  GAA  GTA  TCA  TTG  GAG  GCC  CGA  AGC  TGT  CCC  AGC  AGA  CAC  ACG                1650
Ser  Phe  Glu  Val  Ser  Leu  Glu  Ala  Arg  Ser  Cys  Pro  Ser  Arg  His  Thr
400                      405                     410                      415

GAG  CAT  GTG  TTT  GCC  CTG  CGG  CCG  GTG  GGA  TTC  CGG  GAC  AGC  CTG  GAG                1698
Glu  His  Val  Phe  Ala  Leu  Arg  Pro  Val  Gly  Phe  Arg  Asp  Ser  Leu  Glu
                     420                      425                     430

GTG  GGG  GTC  ACC  TAC  AAC  TGC  ACG  TGC  GGC  TGC  AGC  GTG  GGG  CTG  GAA                1746
Val  Gly  Val  Thr  Tyr  Asn  Cys  Thr  Cys  Gly  Cys  Ser  Val  Gly  Leu  Glu
                     435                      440                     445

CCC  AAC  AGC  GCC  AGG  TGC  AAC  GGG  AGC  GGG  ACC  TAT  GTC  TGC  GGC  CTG                1794
Pro  Asn  Ser  Ala  Arg  Cys  Asn  Gly  Ser  Gly  Thr  Tyr  Val  Cys  Gly  Leu
          450                      455                     460

TGT  GAG  TGC  AGC  CCC  GGC  TAC  CTG  GGC  ACC  AGG  TGC  GAG  TGC  CAG  GAT                1842
Cys  Glu  Cys  Ser  Pro  Gly  Tyr  Leu  Gly  Thr  Arg  Cys  Glu  Cys  Gln  Asp
          465                      470                     475

GGG  GAG  AAC  CAG  AGC  GTG  TAC  CAG  AAC  CTG  TGC  CGG  GAG  GCA  GAG  GGC                1890
Gly  Glu  Asn  Gln  Ser  Val  Tyr  Gln  Asn  Leu  Cys  Arg  Glu  Ala  Glu  Gly
480                      485                     490                      495

AAG  CCA  CTG  TGC  AGC  GGG  CGT  GGG  GAC  TGC  AGC  TGC  AAC  CAG  TGC  TCC                1938
Lys  Pro  Leu  Cys  Ser  Gly  Arg  Gly  Asp  Cys  Ser  Cys  Asn  Gln  Cys  Ser
                     500                      505                     510

TGC  TTC  GAG  AGC  GAG  TTT  GGC  AAG  ATC  TAT  GGG  CCT  TTC  TGT  GAG  TGC                1986
Cys  Phe  Glu  Ser  Glu  Phe  Gly  Lys  Ile  Tyr  Gly  Pro  Phe  Cys  Glu  Cys
                     515                      520                     525

GAC  AAC  TTC  TCC  TGT  GCC  AGG  AAC  AAG  GGA  GTC  CTC  TGC  TCA  GGC  CAT                2034
Asp  Asn  Phe  Ser  Cys  Ala  Arg  Asn  Lys  Gly  Val  Leu  Cys  Ser  Gly  His
          530                      535                     540

GGC  GAG  TGT  CAC  TGC  GGG  GAA  TGC  AAG  TGC  CAT  GCA  GGT  TAC  ATC  GGG                2082
Gly  Glu  Cys  His  Cys  Gly  Glu  Cys  Lys  Cys  His  Ala  Gly  Tyr  Ile  Gly
     545                      550                     555

GAC  AAC  TGT  AAC  TGC  TCG  ACA  GAC  ATC  AGC  ACA  TGC  CGG  GGC  AGA  GAT                2130
Asp  Asn  Cys  Asn  Cys  Ser  Thr  Asp  Ile  Ser  Thr  Cys  Arg  Gly  Arg  Asp
560                      565                     570                      575

GGC  CAG  ATC  TGC  AGC  GAG  CGT  GGG  CAC  TGT  CTC  TGT  GGG  CAG  TGC  CAA                2178
Gly  Gln  Ile  Cys  Ser  Glu  Arg  Gly  His  Cys  Leu  Cys  Gly  Gln  Cys  Gln
                     580                      585                     590

TGC  ACG  GAG  CCG  GGG  GCC  TTT  GGG  GAG  ATG  TGT  GAG  AAG  TGC  CCC  ACC                2226
Cys  Thr  Glu  Pro  Gly  Ala  Phe  Gly  Glu  Met  Cys  Glu  Lys  Cys  Pro  Thr
                     595                      600                     605

TGC  CCG  GAT  GCA  TGC  AGC  ACC  AAG  AGA  GAT  TGC  GTC  GAG  TGC  CTG  CTG                2274
Cys  Pro  Asp  Ala  Cys  Ser  Thr  Lys  Arg  Asp  Cys  Val  Glu  Cys  Leu  Leu
          610                      615                     620

CTC  CAC  TCT  GGG  AAA  CCT  GAC  AAC  CAG  ACC  TGC  CAC  AGC  CTA  TGC  AGG                2322
Leu  His  Ser  Gly  Lys  Pro  Asp  Asn  Gln  Thr  Cys  His  Ser  Leu  Cys  Arg
     625                      630                     635

GAT  GAG  GTG  ATC  ACA  TGG  GTG  GAC  ACC  ATC  GTG  AAA  GAT  GAC  CAG  GAG                2370
Asp  Glu  Val  Ile  Thr  Trp  Val  Asp  Thr  Ile  Val  Lys  Asp  Asp  Gln  Glu
640                      645                     650                      655

GCT  GTG  CTA  TGT  TTC  TAC  AAA  ACC  GCC  AAG  GAC  TGC  GTC  ATG  ATG  TTC                2418
Ala  Val  Leu  Cys  Phe  Tyr  Lys  Thr  Ala  Lys  Asp  Cys  Val  Met  Met  Phe
                     660                      665                     670

ACC  TAT  GTG  GAG  CTC  CCC  AGT  GGG  AAG  TCC  AAC  CTG  ACC  GTC  CTC  AGG                2466
Thr  Tyr  Val  Glu  Leu  Pro  Ser  Gly  Lys  Ser  Asn  Leu  Thr  Val  Leu  Arg
                     675                      680                     685

GAG  CCA  GAG  TGT  GGA  AAC  ACC  CCC  AAC  GCC  ATG  ACC  ATC  CTC  CTG  GCT                2514
```

|  |  |  |  |  |  |  |  |  |  |  |  |  |  |  |  |  |
|---|---|---|---|---|---|---|---|---|---|---|---|---|---|---|---|---|
| Glu | Pro | Glu | Cys | Gly | Asn | Thr | Pro | Asn | Ala | Met | Thr | Ile | Leu | Leu | Ala | |
|  |  | 690 |  |  |  | 695 |  |  |  | 700 |  |  |  |  |  |  |

```
GTG GTC GGT AGC ATC CTC CTT GTT GGG CTT GCA CTC CTG GCT ATC TGG    2562
Val Val Gly Ser Ile Leu Leu Val Gly Leu Ala Leu Leu Ala Ile Trp
    705             710                 715

AAG CTG CTT GTC ACC ATC CAC GAC CGG AGG GAG TTT GCA AAG TTT CAG    2610
Lys Leu Leu Val Thr Ile His Asp Arg Arg Glu Phe Ala Lys Phe Gln
720             725                 730                 735

AGC GAG CGA TCC AGG GCC CGC TAT GAA ATG GCT TCA AAT CCA TTA TAC    2658
Ser Glu Arg Ser Arg Ala Arg Tyr Glu Met Ala Ser Asn Pro Leu Tyr
                740             745                 750

AGA AAG CCT ATC TCC ACG CAC ACT GTG GAC TTC ACC TTC AAC AAG TTC    2706
Arg Lys Pro Ile Ser Thr His Thr Val Asp Phe Thr Phe Asn Lys Phe
            755             760                 765

AAC AAA TCC TAC AAT GGC ACT GTG GAC TGATGTTCC TTCTCCGAGG          2753
Asn Lys Ser Tyr Asn Gly Thr Val Asp
            770             775

GGCTGGAGCG GGGATCTGAT GAAAAGGTCA GACTGAAACG CCTTGCACGG CTGCTCGGCT    2813
TGATCACAGC TCCCTAGGTA GGCACCACAG AGAAGACCTT CTAGTGAGCC TGGGCCAGGA    2873
GCCCACAGTG CTGTACAACA AGGGAAAGGT GCCTGGCCAT GTCACCTGGC TGCTAGCCAG    2933
AGCCATGCCA GGTTCGCGTC CCTAAGAGCT TGGGATAAAG CAAGGGGACC TTGGCGCTCT    2993
CAGCTTTCCC TGCCACATCC AGCTTGTTGT CCCAATGAAA TACTGAGATG CTGGGCTGTC    3053
TCTCCTTCC AGGAATCGTG GGCCCCAGC CTGGCCAGAC AAGAAGACTG TCAGGAAGGG      3113
TCGGAGTCTG TAAAACCAGC ATACAGTTTG GCTTTTTCA CATTGATCAT TTTTATATGA    3173
AATAAAAAGA TCCTGCATTT ATGGTGTAGT TCTGAGTCCT GAGACTTTTC TGCGTGATGC    3233
TATGCCTTGC ACACAGGTGT TGGTGATGGG GCTGTTGAGA TGCCTGTTGA AGGTACATCG    3293
TTTGCAAATG TCAGTTTCCT CTCCTGTCCG TGTTTGTTTA GTACTTTTAT AATGAAAAGA    3353
AACAAGATTG TTTGGGATTG GAAGTAAAGA TTAAAACCAA AAGAATTTGT GTTTGTCTGC    3413
CC                                                                  3415
```

( 2 ) INFORMATION FOR SEQ ID NO:2:

( i ) SEQUENCE CHARACTERISTICS:
        ( A ) LENGTH: 799 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Pro Arg Ala Pro Ala Pro Leu Tyr Ala Cys Leu Leu Gly Leu Cys
-23         -20             -15                 -10

Ala Leu Leu Pro Arg Leu Ala Gly Leu Asn Ile Cys Thr Ser Gly Ser
        -5              1               5

Ala Thr Ser Cys Glu Glu Cys Leu Leu Ile His Pro Lys Cys Ala Trp
10              15              20              25

Cys Ser Lys Glu Asp Phe Gly Ser Pro Arg Ser Ile Thr Ser Arg Cys
            30              35              40

Asp Leu Arg Ala Asn Leu Val Lys Asn Gly Cys Gly Gly Glu Ile Glu
            45              50              55

Ser Pro Ala Ser Ser Phe His Val Leu Arg Ser Leu Pro Leu Ser Ser
        60              65              70

Lys Gly Ser Gly Ser Ala Gly Trp Asp Val Ile Gln Met Thr Pro Gln
75              80              85
```

| | | | | | | | | | | | | | | |
|---|---|---|---|---|---|---|---|---|---|---|---|---|---|---|
| Glu | Ile | Ala | Val | Asn | Leu | Arg | Pro | Gly | Asp | Lys | Thr | Thr | Phe | Gln | Leu |
| 90 | | | | | 95 | | | | 100 | | | | | | 105 |
| Gln | Val | Arg | Gln | Val | Glu | Asp | Tyr | Pro | Val | Asp | Leu | Tyr | Tyr | Leu | Met |
| | | | | 110 | | | | | 115 | | | | | 120 | |
| Asp | Leu | Ser | Leu | Ser | Met | Lys | Asp | Asp | Leu | Asp | Asn | Ile | Arg | Ser | Leu |
| | | | | 125 | | | | 130 | | | | | 135 | | |
| Gly | Thr | Lys | Leu | Ala | Glu | Glu | Met | Arg | Lys | Leu | Thr | Ser | Asn | Phe | Arg |
| | | | 140 | | | | | 145 | | | | | 150 | | |
| Leu | Gly | Phe | Gly | Ser | Phe | Val | Asp | Lys | Asp | Ile | Ser | Pro | Phe | Ser | Tyr |
| | | 155 | | | | | 160 | | | | 165 | | | | |
| Thr | Ala | Pro | Arg | Tyr | Gln | Thr | Asn | Pro | Cys | Ile | Gly | Tyr | Lys | Leu | Phe |
| 170 | | | | | 175 | | | | | 180 | | | | | 185 |
| Pro | Asn | Cys | Val | Pro | Ser | Phe | Gly | Phe | Arg | His | Leu | Leu | Pro | Leu | Thr |
| | | | | 190 | | | | | 195 | | | | | 200 | |
| Asp | Arg | Val | Asp | Ser | Phe | Asn | Glu | Glu | Val | Arg | Lys | Gln | Arg | Val | Ser |
| | | | | 205 | | | | | 210 | | | | | 215 | |
| Arg | Asn | Arg | Asp | Ala | Pro | Glu | Gly | Gly | Phe | Asp | Ala | Val | Leu | Gln | Ala |
| | | | 220 | | | | | 225 | | | | | 230 | | |
| Ala | Val | Cys | Lys | Glu | Lys | Ile | Gly | Trp | Arg | Lys | Asp | Ala | Leu | His | Leu |
| | 235 | | | | | 240 | | | | | 245 | | | | |
| Leu | Val | Phe | Thr | Thr | Asp | Asp | Val | Pro | His | Ile | Ala | Leu | Asp | Gly | Lys |
| 250 | | | | | 255 | | | | | 260 | | | | | 265 |
| Leu | Gly | Gly | Leu | Val | Gln | Pro | His | Asp | Gly | Gln | Cys | His | Leu | Asn | Glu |
| | | | | 270 | | | | 275 | | | | | 280 | | |
| Ala | Asn | Glu | Tyr | Thr | Ala | Ser | Asn | Gln | Met | Asp | Tyr | Pro | Ser | Leu | Ala |
| | | | 285 | | | | | 290 | | | | | 295 | | |
| Leu | Leu | Gly | Glu | Lys | Leu | Ala | Glu | Asn | Asn | Ile | Asn | Leu | Ile | Phe | Ala |
| | | | 300 | | | | | 305 | | | | | 310 | | |
| Val | Thr | Lys | Asn | His | Tyr | Met | Leu | Tyr | Lys | Asn | Phe | Thr | Ala | Leu | Ile |
| | 315 | | | | | 320 | | | | | 325 | | | | |
| Pro | Gly | Thr | Thr | Val | Glu | Ile | Leu | Asp | Gly | Asp | Ser | Lys | Asn | Ile | Ile |
| 330 | | | | | 335 | | | | | 340 | | | | | 345 |
| Gln | Leu | Ile | Ile | Asn | Ala | Tyr | Asn | Ser | Ile | Arg | Ser | Lys | Val | Glu | Leu |
| | | | | 350 | | | | | 355 | | | | | 360 | |
| Ser | Val | Trp | Asp | Gln | Pro | Glu | Asp | Leu | Asn | Leu | Phe | Phe | Thr | Ala | Thr |
| | | | 365 | | | | | 370 | | | | | 375 | | |
| Cys | Gln | Asp | Gly | Val | Ser | Tyr | Pro | Gly | Gln | Arg | Lys | Cys | Glu | Gly | Leu |
| | | | 380 | | | | | 385 | | | | | 390 | | |
| Lys | Ile | Gly | Asp | Thr | Ala | Ser | Phe | Glu | Val | Ser | Leu | Glu | Ala | Arg | Ser |
| | 395 | | | | | 400 | | | | | 405 | | | | |
| Cys | Pro | Ser | Arg | His | Thr | Glu | His | Val | Phe | Ala | Leu | Arg | Pro | Val | Gly |
| 410 | | | | | 415 | | | | | 420 | | | | | 425 |
| Phe | Arg | Asp | Ser | Leu | Glu | Val | Gly | Val | Thr | Tyr | Asn | Cys | Thr | Cys | Gly |
| | | | | 430 | | | | | 435 | | | | | 440 | |
| Cys | Ser | Val | Gly | Leu | Glu | Pro | Asn | Ser | Ala | Arg | Cys | Asn | Gly | Ser | Gly |
| | | | 445 | | | | | 450 | | | | | 455 | | |
| Thr | Tyr | Val | Cys | Gly | Leu | Cys | Glu | Cys | Ser | Pro | Gly | Tyr | Leu | Gly | Thr |
| | | | 460 | | | | 465 | | | | | 470 | | | |
| Arg | Cys | Glu | Cys | Gln | Asp | Gly | Glu | Asn | Gln | Ser | Val | Tyr | Gln | Asn | Leu |
| | 475 | | | | | 480 | | | | | 485 | | | | |
| Cys | Arg | Glu | Ala | Glu | Gly | Lys | Pro | Leu | Cys | Ser | Gly | Arg | Gly | Asp | Cys |
| 490 | | | | | 495 | | | | | 500 | | | | | 505 |
| Ser | Cys | Asn | Gln | Cys | Ser | Cys | Phe | Glu | Ser | Glu | Phe | Gly | Lys | Ile | Tyr |
| | | | | 510 | | | | | 515 | | | | | 520 | |

```
Gly Pro Phe Cys Glu Cys Asp Asn Phe Ser Cys Ala Arg Asn Lys Gly
            525                 530                 535

Val Leu Cys Ser Gly His Gly Glu Cys His Cys Gly Glu Cys Lys Cys
            540                 545                 550

His Ala Gly Tyr Ile Gly Asp Asn Cys Asn Cys Ser Thr Asp Ile Ser
            555                 560                 565

Thr Cys Arg Gly Arg Asp Gly Gln Ile Cys Ser Glu Arg Gly His Cys
570             575                 580                     585

Leu Cys Gly Gln Cys Gln Cys Thr Glu Pro Gly Ala Phe Gly Glu Met
            590                 595                 600

Cys Glu Lys Cys Pro Thr Cys Pro Asp Ala Cys Ser Thr Lys Arg Asp
            605                 610                 615

Cys Val Glu Cys Leu Leu Leu His Ser Gly Lys Pro Asp Asn Gln Thr
            620                 625                 630

Cys His Ser Leu Cys Arg Asp Glu Val Ile Thr Trp Val Asp Thr Ile
            635                 640                 645

Val Lys Asp Asp Gln Glu Ala Val Leu Cys Phe Tyr Lys Thr Ala Lys
650             655                 660                     665

Asp Cys Val Met Met Phe Thr Tyr Val Glu Leu Pro Ser Gly Lys Ser
            670                 675                 680

Asn Leu Thr Val Leu Arg Glu Pro Glu Cys Gly Asn Thr Pro Asn Ala
            685                 690                 695

Met Thr Ile Leu Leu Ala Val Val Gly Ser Ile Leu Leu Val Gly Leu
            700                 705                 710

Ala Leu Leu Ala Ile Trp Lys Leu Leu Val Thr Ile His Asp Arg Arg
            715                 720                 725

Glu Phe Ala Lys Phe Gln Ser Glu Arg Ser Arg Ala Arg Tyr Glu Met
730             735                 740                     745

Ala Ser Asn Pro Leu Tyr Arg Lys Pro Ile Ser Thr His Thr Val Asp
            750                 755                 760

Phe Thr Phe Asn Lys Phe Asn Lys Ser Tyr Asn Gly Thr Val Asp
            765                 770                 775
```

(2) INFORMATION FOR SEQ ID NO:3:

(i) SEQUENCE CHARACTERISTICS:
        (A) LENGTH: 12 amino acids
        (B) TYPE: amino acid
        (D) TOPOLOGY: unknown (xi) SEQUENCE DESCRIPTION: SEQ ID NO:3:

```
Asp Leu Tyr Tyr Leu Met Asp Leu Ser Tyr Ser Met
1               5                   10
```

(2) INFORMATION FOR SEQ ID NO:4:

(i) SEQUENCE CHARACTERISTICS:
        (A) LENGTH: 6 amino acids
        (B) TYPE: amino acid
        (D) TOPOLOGY: unknown (xi) SEQUENCE DESCRIPTION: SEQ ID NO:4:

```
Gly Leu Asn Ile Cys Thr
1               5
```

(2) INFORMATION FOR SEQ ID NO:5:

(i) SEQUENCE CHARACTERISTICS:
        (A) LENGTH: 6 amino acids (B) TYPE: amino acid
(D) TOPOLOGY: unknown (xi) SEQUENCE DESCRIPTION: SEQ ID NO:5:

Xaa Leu Asn Ile Cys Thr
1                5

(2) INFORMATION FOR SEQ ID NO:6:

(i) SEQUENCE CHARACTERISTICS:
(A) LENGTH: 21 amino acids
(B) TYPE: amino acid
(D) TOPOLOGY: unknown (xi) SEQUENCE DESCRIPTION: SEQ ID NO:6:

Cys Thr His Thr Val Asp Phe Thr Phe Asn Lys Phe Asn Lys Ser Tyr
1                5                       10                      15

Asn Gly Thr Val Asp
               20

(2) INFORMATION FOR SEQ ID NO:7:

(i) SEQUENCE CHARACTERISTICS:
(A) LENGTH: 6 amino acids
(B) TYPE: amino acid
(D) TOPOLOGY: unknown (xi) SEQUENCE DESCRIPTION: SEQ ID NO:7:

Gly Pro Asn Ile Cys Thr
1                5